United States Patent
Hwang et al.

(10) Patent No.: US 9,834,493 B2
(45) Date of Patent: Dec. 5, 2017

(54) PROCESS FOR REDUCING THE BENZENE CONTENT OF GASOLINE BY ALKYLATING BENZENE USING A LOWER OLEFIN IN THE PRESENCE OF A PARAFFINIC DILUENT

(75) Inventors: Shyh-Yuan H. Hwang, Needham, MA (US); Ronald Birkhoff, Houston, TX (US); Richard F. Guarino, Fairhaven, MA (US); J. Erik Moy, South Grafton, MA (US); Geeta Pherwani, Watertown, MA (US)

(73) Assignee: BADGER LICENSING LLC, Boston, MA (US)

( * ) Notice: Subject to any disclaimer, the term of this patent is extended or adjusted under 35 U.S.C. 154(b) by 248 days.

(21) Appl. No.: 13/982,956

(22) PCT Filed: Feb. 7, 2011

(86) PCT No.: PCT/US2011/023904
§ 371 (c)(1),
(2), (4) Date: Aug. 23, 2013

(87) PCT Pub. No.: WO2012/108861
PCT Pub. Date: Aug. 16, 2012

(65) Prior Publication Data
US 2013/0331627 A1  Dec. 12, 2013

(51) Int. Cl.
*C07C 2/66* (2006.01)
*C10G 29/20* (2006.01)
*C10L 1/06* (2006.01)

(52) U.S. Cl.
CPC .............. *C07C 2/66* (2013.01); *C10G 29/205* (2013.01); *C10L 1/06* (2013.01);
(Continued)

(58) Field of Classification Search
CPC  C07C 2/66; C10G 29/205; C10G 2300/1088; C10G 2300/1044; C10G 2300/301; C10G 2400/02; C10L 1/06
(Continued)

(56) References Cited

U.S. PATENT DOCUMENTS

| | | |
|---|---|---|
| 3,775,483 A | 11/1973 | Frederickson et al. |
| 4,343,957 A | 8/1982 | Sartorio et al. |

(Continued)

FOREIGN PATENT DOCUMENTS

| | | |
|---|---|---|
| EP | 0485683 A1 | 11/1990 |
| WO | 2012108924 A1 | 8/2012 |

(Continued)

OTHER PUBLICATIONS

1990 Clean Air Act US Code (CAA 101-618 or 42 USC 7401-7671).*

(Continued)

*Primary Examiner* — In Suk Bullock
*Assistant Examiner* — Jason Chong
(74) *Attorney, Agent, or Firm* — Roberts Mlotkowski Safran Cole & Calderon P.C.

(57) ABSTRACT

A process for reducing the benzene content of gasoline stream, such as a reformate or light naphtha, comprises alkylating the gasoline stream in a reaction zone with an olefin alkylating agent. A paraffinic stream comprising C5 to C10 paraffins is fed to the inlet of the alkylation reaction zone.

10 Claims, 1 Drawing Sheet

(52) U.S. Cl.
CPC ............... *C10G 2300/1044* (2013.01); *C10G 2300/1088* (2013.01); *C10G 2300/301* (2013.01); *C10G 2300/802* (2013.01); *C10G 2400/02* (2013.01)

(58) Field of Classification Search
USPC ........................................................ 585/467
See application file for complete search history.

(56) References Cited

U.S. PATENT DOCUMENTS

| | | | |
|---|---|---|---|
| 4,393,262 | A | 7/1983 | Kaeding |
| 4,891,458 | A | 1/1990 | Innes et al. |
| 4,950,823 | A | 8/1990 | Harandi et al. |
| 5,149,894 | A | 9/1992 | Holtemrann et al. |
| 5,157,158 | A | 10/1992 | Berna Tejero et al. |
| 5,491,270 | A | 2/1996 | Chin et al. |
| 5,545,788 | A | 8/1996 | Cheng et al. |
| 6,008,422 | A | 12/1999 | Schulz et al. |
| 6,835,862 | B1 | 12/2004 | Gajda et al. |
| 7,396,968 | B1 * | 7/2008 | Sohn et al. ............ 585/450 |
| 7,476,774 | B2 | 1/2009 | Umansky et al. |
| 7,576,247 | B2 * | 8/2009 | Sohn ................. C07C 2/66 585/323 |
| 2006/0194999 | A1 | 8/2006 | Brown et al. |
| 2008/0171900 | A1 | 7/2008 | Scmidt |
| 2010/0004497 | A1 * | 1/2010 | Glover ............... C07C 2/66 585/323 |
| 2010/0210886 | A1 | 8/2010 | Brown et al. |
| 2010/0249472 | A1 | 9/2010 | Clark et al. |
| 2010/0300930 | A1 | 12/2010 | Clark et al. |

FOREIGN PATENT DOCUMENTS

| | | |
|---|---|---|
| WO | 2012108926 A1 | 8/2012 |
| WO | 2013028215 A1 | 2/2013 |

OTHER PUBLICATIONS

Laredo G C et al.: "Benzene reduction in gasoline by alkylation with olefins: Effect of the experimental conditions on 1 the product selectivity", Applied Catalysis A: General, Elsevier Science, Amsterdam, NL vol. 384, No. 1-2, Aug. 20, 2010, pp. 115-121.
Umansky B et al.: "Banish the benzene, boost the octane", Hydrocarbon Engineering, Palladian Publications, Farnham, GB, vol. 12, Jan. 1, 2007, pp. 61-62.
El-Mekki El Malki, Michael Clark: "BenzOUT Reducing Benzene Enhancing Gasoline Product Value", NPRA Conference, Phoenix, AZ, Mar. 21-23, 2010; XP00263231 1.
Pierre Leprince: "Le raffinage du petrole—3.Procédés de Transformation", Jan. 1, 1998, Technip, Paris, XP002670362, vol. 3.
The International Search Report and the Written Opinion of the International Searching Authority issued in related international application No. PCT/US2011/062626.
The International Search Report and the Written Opinion of the International Searching Authority issued in corresponding international application No. PCT/US2011/023904.
The International Search Report and the Written Opinion of the International Searching Authority issued in related international application No. PCT/US2011/062635.
The International Search Report and the Written Opinion of the International Searching Authority issued in related international application No. PCT/US2011/062648.

* cited by examiner

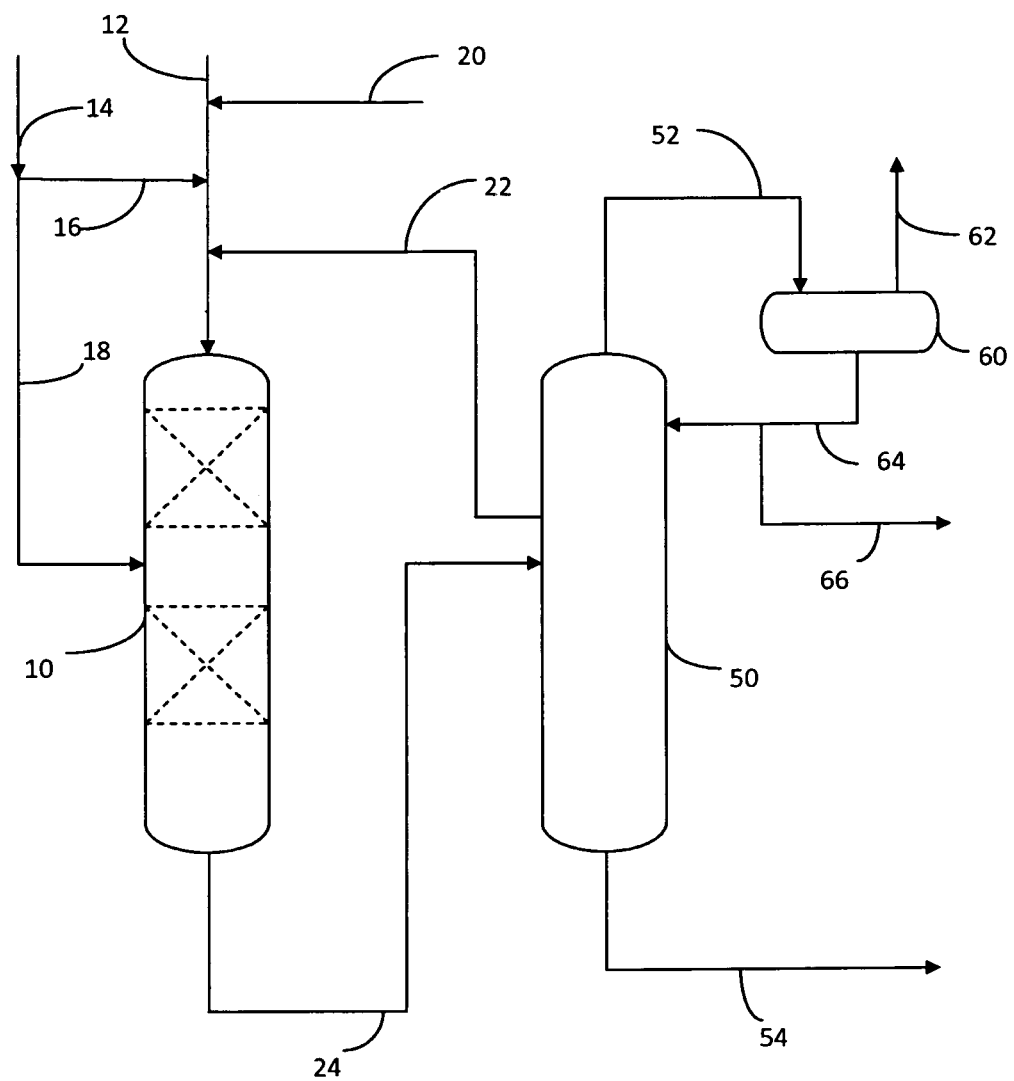

PROCESS FOR REDUCING THE BENZENE CONTENT OF GASOLINE BY ALKYLATING BENZENE USING A LOWER OLEFIN IN THE PRESENCE OF A PARAFFINIC DILUENT

CROSS-REFERENCE TO RELATED APPLICATIONS

The present Application is a U.S. National Phase of international application PCT/US2011/023904 filed on Feb. 7, 2011. The disclosure of the PCT Application is hereby incorporated by reference into the present Application.

FIELD

This invention relates to a process for reducing the benzene content of gasoline.

BACKGROUND

Benzene is considered to be environmentally hazardous. As a result, the State of California and the United States Environmental Protection Agency have instituted regulations to limit the amount of benzene which may be present in gasoline. As of January 2011, the US MSAT-2 (Mobile Source Air Toxics) regulation requires reduction of this annual average benzene content in gasoline to no greater than 0.62 volume %.

One known route for reducing the benzene content of gasoline is to selectively alkylate the benzene using a lower olefin. For example, Holtermann et al U.S. Pat. No. 5,149,894 describes a process for converting benzene to alkylated benzenes in a gasoline blend stock. The process involves contacting a benzene-containing gasoline blend stock with a C2 to C4 olefin stream in the presence of a catalyst containing the zeolite, SSZ-25, to produce an alkylated light hydrocarbon stream with reduced benzene content.

Cheng et al. U.S. Pat. No. 5,545,788 describes a process for the production of a more environmentally suitable gasoline by removing a substantial portion of benzene in gasoline by alkylation of reformate. The process involves alkylation using a light olefin feed at low temperature over the zeolite catalyst, MCM-49.

Umansky el al. U.S. Pat. No. 7,476,774 describes a process where light olefins including ethylene and propylene are extracted from refinery off-gases, such as from a catalytic cracking unit, into a light aromatic stream, such as a reformate containing benzene and other single ring aromatic compounds, which is then reacted with the light olefins to form a gasoline boiling range product containing alkylaromatics. The alkylation reaction is carried out in the liquid phase with a catalyst which preferably comprises a member of the MWW family of zeolites, such as MCM-22, using a fixed catalyst bed.

When benzene, such as that contained in a gasoline feed, is alkylated with an olefin in the liquid phase over a fixed bed catalyst, the reaction is highly exothermic, with an adiabatic temperature rise across the reactor. The maximum temperature rise across the reactor is set by practical limitations determined by the difference between the minimum reactor inlet temperature required for reaction, and the maximum outlet temperature which is deemed practical for the mechanical design of the reactor system.

To control the temperature rise, the quantity of olefin to each reactor stage is limited. In applications where the concentration of benzene in the refinery stream is relatively high, for example 20 volume % and above, the temperature limitation in an adiabatic process, according to current technology, requires that at least four stages in series are used, in order to be able to limit and distribute the olefin. The use of such a large number of reactors increases the cost of the plant substantially.

According to the present invention, it has now been found that the problem of the adiabatic temperature rise during the alkylation of a benzene-containing gasoline stream, such as a reformate or light naphtha, with an olefin alkylating agent can be reduced by diluting the feed to the alkylation reactor with a C5 to C10 paraffin stream. This problem of adiabatic temperature rise is more pronounced in a single phase system. i.e. vapor phase or liquid phase, as opposed to a mixed phase system including both a vapor phase and a liquid phase.

SUMMARY

In an alkylation process, benzene contained in a refinery gasoline stream is alkylated. The alkylation process comprises contacting said refinery gasoline stream with an alkylating agent comprising one or more C2 to C5 olefins in an alkylation reaction zone under alkylation conditions to produce an alkylated effluent. The alkylation reaction zone comprises at least one alkylation reaction stage. A paraffinic stream comprising C5 to C10 hydrocarbons is fed to the inlet of at least one of the alkylation reaction stages.

The paraffinic stream may comprise less than 2.0 wt % aromatics and/or olefins.

The refinery gasoline stream may be, for example, a reformate or a light naphtha. The alkylating agent may be, for example, propylene or a mixture of propylene and propane.

The refinery gasoline stream may comprise at least 10 volume % benzene. The refinery gasoline stream may be substantially in the liquid phase during contact of the refinery gasoline stream with the alkylating agent in the alkylation reaction zone.

The contact of the refinery gasoline stream with the alkylating agent in the alkylation reaction zone may take place under substantially adiabatic conditions.

The refinery gasoline stream may be a reformate or a light naphtha. The paraffinic stream may be a distillation product obtained by distilling the alkylated effluent from the reaction zone.

The alkylated effluent may comprise less than 2.0 volume % benzene, for example, less than 0.62 volume % benzene.

The alkylated effluent may comprise no more than 2 volume % of compounds having a boiling point greater than 236° C. at atmospheric pressure.

The alkylation reaction may take place over a catalyst comprising an MWW zeolite.

BRIEF DESCRIPTION OF THE DRAWING

FIG. 1 is a schematic diagram of one embodiment of a process for alkylating a benzene containing feedstock.

DETAILED DESCRIPTION

Refinery streams which may be alkylated to decrease benzene content include streams comprising benzene and alkylbenzenes. Examples of such streams include reformates and naphtha streams, especially light naphtha streams. Blends of refinery streams may also be alkylated. The refinery streams employed in the present process typically comprise at least 10 wt %, such as about 15 wt % to about 20 wt %, benzene.

Reformates have high octane number attributable to their high aromatics content. However, high concentrations of benzene in reformate, e.g., 4 to 6 wt %, can limit reformate utility as a blending component where environmental considerations require low benzene levels in gasoline product. Various efforts to reduce benzene content in reformate, e.g., selective hydrogenation, high temperature fluid-bed MBR, and reformate alkylation with methanol all suffer from octane losses or total liquid product losses associated with undesired cracking of C5+ non-aromatics.

The present invention relates to a process whereby benzene-containing reformates and other refinery streams are treated to reduce benzene content by alkylation. Undesirable alkylation of higher boiling aromatics, such as xylenes, may be minimized.

Examples of suitable alkylating agents for use in the present process are olefins having 2 to 5 carbon atoms, such as ethylene, propylene, butenes, and pentenes. Mixtures of light olefins are especially useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, and FCC off-gas, etc., are useful alkylating agents herein. Compositions of examples of olefin containing streams suitable for use as alkylating agents are described, for example, in U.S. Pat. No. 7,476,774.

In addition to the olefinic alkylating agent and the benzene-containing refinery stream, in the present process a paraffinic stream comprising C5 to C10 hydrocarbons is fed to the alkylation reactor, typically in amount such that the weight ratio of paraffinic stream to benzene-containing refinery stream is between about 0.25 and about 4. Generally, the paraffinic stream contains less than 2.0 wt % aromatics and/or olefins. In one embodiment, the refinery gasoline stream is a light reformate, and wherein said paraffinic stream is a distillation product obtained by distilling the alkylated effluent from the alkylation reaction.

The alkylation process may be conducted such that the organic reactants, i.e., the alkylatable aromatic compound, the alkylating agent and the paraffinic stream, are brought into contact with a zeolite catalyst composition in a suitable reaction zone, such as, for example, in a flow reactor containing a fixed bed of the catalyst composition, under effective alkylation conditions. Such conditions may include a temperature of from about 0° C. to about 500° C., for example, between about 50° C. and about 300° C., and a pressure of from about 0.2 to about 250 atmospheres, for example, from about 1 to about 50 atmospheres. The feed weight hourly space velocity (WHSV) will generally be between 0.1 hr$^{-1}$ and 500 hr$^{-1}$, for example, from 0.5 hr$^{-1}$ to 100 hr$^{-1}$. The latter WHSV is based upon the total weight of active catalyst (and binder if present). The reaction may be conducted under substantially adiabatic conditions.

The reactants may be in the vapor phase or the liquid phase or in a mixture of liquid and vapor phases. The reactants may be neat, i.e., free from intentional admixture or dilution with other material, or they can be brought into contact with the zeolite catalyst composition with the aid of carrier gases or diluents such as, for example, hydrogen or nitrogen.

The alkylation reaction zone may comprise one or more alkylation reaction stages. When more than one alkylation stage is used, fresh refinery gasoline feed or fresh alkylating agent feed may, optionally, be introduced between one or more stages.

Catalyst System

The catalyst system used in the alkylation of the present process is preferably one based on a zeolite of the MWW family because these catalysts exhibit excellent activity for the desired aromatic alkylation reaction using light olefins, especially propylene. It is, however, possible to use other molecular sieve catalysts for this alkylation, including catalysts based on ZSM-12 as described in U.S. Pat. Nos. 3,755,483 and 4,393,262 for the manufacture of petrochemical cumene from refinery benzene and propylene or catalysts based on zeolite beta as described in U.S. Pat. No. 4,891,458, all of which are reported to have activity for the alkylation of light aromatics by propylene.

MWW Zeolite

The MWW family of zeolite materials has achieved recognition as having a characteristic framework structure which presents unique and interesting catalytic properties. The MWW topology consists of two independent pore systems: a sinusoidal ten-member ring [10 MR] two dimensional channel separated from each other by a second, two dimensional pore system comprised of 12 MR super cages connected to each other through 10 MR windows. The crystal system of the MWW framework is hexagonal and the molecules diffuse along the [100] directions in the zeolite, i.e., there is no communication along the c direction between the pores. In the hexagonal plate-like crystals of the MWW type zeolites, the crystals are formed of relatively small number of units along the c direction as a result of which, much of the catalytic activity is due to active sites located on the external surface of the crystals in the form of the cup-shaped cavities. In the interior structure of certain members of the family such as MCM-22, the cup-shaped cavities combine together to form a supercage. The MCM-22 family of zeolites has attracted significant scientific attention since its initial announcement by Leonovicz et al. in Science 264, 1910-1913 [1994] and the later recognition that the family includes a number of zeolitic materials such as PSH 3, MCM-22, MCM-49, MCM-56, SSZ-25, ERB-1, ITQ-1, and others. Lobo et al. A1ChE Annual Meeting 1999, Paper 292J.

The relationship between the various members of the MCM-22 family have been described in a number of publications. Significant members of the family are MCM-22, MCM-36, MCM-49, and MCM-56. When initially synthesized from a mixture including sources of silica, alumina, sodium, and hexamethylene imine as an organic template, the initial product will be MCM-22 precursor or MCM-56, depending upon the silica:alumina ratio of the initial synthesis mixture. At silica:alumina ratios greater than 20, MCM-22 precursor comprising H-bonded vertically aligned layers is produced whereas randomly oriented, non-bonded layers of MCM-56 are produced at lower silica:alumina ratios. Both these materials may be converted to a swollen material by the use of a pillaring agent and on calcination, this leads to the laminar, pillared structure of MCM-36. The as-synthesized MCM-22 precursor can be converted directly by calcination to MCM-22 which is identical to calcined MCM-49, an intermediate product obtained by the crystallization of the randomly oriented, as-synthesized MCM-56. In MCM-49, the layers are covalently bonded with an interlaminar spacing slightly greater than that found in the calcined MCM-22/MCM-49 materials. The as-synthesized MCM-56 may be calcined itself to form calcined MCM-56 which is distinct from calcined MCM-22/MCM-49 in having a randomly oriented rather than a laminar structure. In the patent literature MCM-22 is described in U.S. Pat. No. 4,954,325 as well as in U.S. Pat. Nos. 5,250,777; 5,284,643 and 5,382,742. MCM-49 is described in U.S. Pat. No. 5,236,575; MCM-36 in U.S. Pat. No. 5,229,341 and MCM-56 in U.S. Pat. No. 5,362,697.

A preferred zeolitic material for use as the MWW component of the catalyst system is MCM-22.

Catalyst Matrix

In addition to the zeolitic component, the catalyst will usually contain a matrix material or binder in order to give adequate strength to the catalyst as well as to provide the desired porosity characteristics in the catalyst. High activity catalysts may, however, be formulated in the binder-free form by the use of suitable extrusion techniques, for example, as described in U.S. Pat. No. 4,908,120. When used, matrix materials suitably include alumina, silica, silica alumina, titania, zirconia, and other inorganic oxide materials commonly used in the formulation of molecular sieve catalysts. For use in the present process, the level of zeolite, such as MCM-22 or ZSM-5 type (intermediate pore size) zeolite, in the finished matrixed catalyst will be typically from 20 to 70% by weight, and in most cases from 25 to 65% by weight. In manufacture of a matrixed catalyst, the active ingredient will typically be mulled with the matrix material using an aqueous suspension of the catalyst and matrix, after which the active component and the matrix are extruded into the desired shape, for example, cylinders, hollow cylinders, trilobe, quadlobe, etc. A binder material such as clay may be added during the mulling in order to facilitate extrusion, increase the strength of the final catalytic material and to confer other desirable solid state properties. The amount of clay will not normally exceed 10% by weight of the total finished catalyst. Unbound (or, alternatively, self-bound) catalysts are suitably produced by the extrusion method described in U.S. Pat. No. 4,582,815, to which reference is made for a description of the method and of the extruded products obtained by its use. The method described there enables extrudates having high constraining strength to be produced on conventional extrusion equipment and accordingly, the method is suitable for producing the catalysts which are silica-rich. The catalysts are produced by mulling the zeolite with water to a solids level of 25 to 75 wt % in the presence of 0.25 to 10 wt % of basic material such as sodium hydroxide. Further details are to be found in U.S. Pat. No. 4,582,815.

Gasoline Product

Even with a refinery gasoline feed comprising at least 10 volume % benzene, the present process allows the production of a gasoline product which contains less than 2 volume %, typically less than 0.62 volume %, benzene and generally no more than 2 volume % of compounds having a boiling point greater than 236° C. at atmospheric pressure.

The invention will now be more particularly described with reference to the following non-limiting Examples.

Example

As shown in FIG. 1, a benzene containing feed, such as a light reformate, is introduced into an alkylation reactor 10 via line 12. In FIG. 1, alkylation reactor 10 is illustrated as a two stage reactor. However, it will be understood that alkylation reactor 10 may also have a single alkylation stage or more than two alkylation stages.

In FIG. 1, an olefin feed, such as a propylene feed, from line 14 is split into line 16 and 18. Line 16 combines olefin feed with the benzene containing feed of line 12 upstream of the alkylation reactor 10. Line 18 introduces olefin feed at a midpoint of the alkylation reactor 10, e.g., at a point between a first reaction stage and a second reaction stage. Although FIG. 1 illustrates splitting of the olefin feed and introduction of the olefin feed into the alkylation reactor 10 at two points, it will be understood that other reactor configurations are possible. For example, all of the olefin feed may be introduced to the beginning of the first alkylation stage along with the benzene containing feed through the same or different lines.

In one embodiment, a paraffinic stream comprising C5 to C10 hydrocarbons is combined with the benzene containing feed in line 12 via line 20. The paraffinic stream in line 20 may be an externally provided refinery stream, such as a light naphtha stream. In another embodiment, an internally provided paraffinic stream comprising C5 to C10 hydrocarbons is introduced into line 12 via line 22. This internally provided stream is taken as a side draw from stabilizer column 50 as described below. Although not shown in FIG. 1, it will be understood that other configurations for introducing a paraffinic stream into alkylation reactor are possible. For example, lines 20 and 22 may pass directly into the beginning of the first alkylation stage of the alkylation reactor, instead of into line 12.

Effluent from alkylation reactor 10 is passed via line 24 to stabilizer column 50. As mentioned above, a paraffinic stream comprising C5 to C10 hydrocarbons may be taken as a side draw from stabilizer column 50 via line 22 to be introduced into alkylation reactor 10. Optionally, however, line 22 may be omitted and all of the paraffinic cofeed introduced into the alkylation reactor 10 may come from an external source via line 20.

The overhead stream from the stabilizer column 50 includes light paraffins, such as paraffins having less than five carbon atoms. This overhead may also comprise unreacted olefins, if any, in the effluent stream from the alkylation reactor 10. This overhead stream passes from stabilizer column 50 to condenser 60 via line 52.

Vent gas may be removed via line 62. The condensate from condenser 60 may be recycled to the stabilizer column 50 via line 64. A portion of this condensate may also be taken from line 64 and recovered via line 66, for example, as a liquefied petroleum gas (LPG).

The alkylated product with reduced benzene content is recovered from the stabilizer column via line 54.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for alkylating benzene contained in a refinery gasoline stream, said process comprising contacting said refinery gasoline stream with an alkylating agent comprising one or more C2 to C5 olefins in an alkylation reaction zone under alkylation conditions to produce an alkylated effluent, wherein said alkylation reaction zone comprises at least one alkylation reaction stage, wherein a paraffinic stream comprising C5 to C10 hydrocarbons and less than 2.0 wt % aromatics and olefins is fed to the inlet of said at least one of the alkylation reaction stage, and wherein said paraffinic stream is a distillation product obtained by distilling the alkylated effluent from the alkylation reaction zone.

2. A process according to claim 1, wherein said refinery gasoline stream comprises at least 10 volume % benzene.

3. A process according to claim 1, wherein said refinery gasoline stream is substantially in the liquid phase during said contacting.

4. A process according to claim 1, wherein said contacting takes place under substantially adiabatic conditions.

5. A process according to claim 1, wherein said refinery gasoline stream is a reformate comprising C5 to C10 hydrocarbons.

6. A process according to claim 1, wherein said alkylating agent is propylene.

7. A process according to claim 1, wherein said alkylated effluent comprises less than 2.0 volume % benzene.

8. A process according to claim 1, wherein said alkylated effluent comprises no more than 2 volume % of compounds having a boiling point greater than 236° C. at atmospheric pressure.

9. A process according to claim 1, wherein the alkylation reaction takes place over a catalyst comprising an MWW zeolite.

10. A process according to claim 1, wherein said alkylated effluent comprises less than 0.62 volume % benzene.

* * * * *